United States Patent [19]

Okuyama et al.

[11] Patent Number: 5,414,073
[45] Date of Patent: May 9, 1995

[54] PRADIMIC ACIDS, AMIDES, AND NOVEL PRADIMICIN DERIVATIVES

[75] Inventors: Satsuki Okuyama, Hachioji; Takaaki Okita, Tokyo; Hajime Kamachi, Urayasu, all of Japan

[73] Assignee: Bristol-Myers Squibb, New York, N.Y.

[21] Appl. No.: 285,327

[22] Filed: Aug. 3, 1994

Related U.S. Application Data

[60] Continuation of Ser. No. 214,909, Mar. 17, 1994, abandoned, which is a division of Ser. No. 914,908, Jul. 16, 1992, Pat. No. 5,326,867.

[51] Int. Cl.⁶ ..................... A61K 31/70; C07H 15/24
[52] U.S. Cl. ..................... 536/18.5; 536/6.4; 536/16.8; 536/17.2; 536/18.1
[58] Field of Search ........... 536/6.4, 16.8, 17.2, 536/18.1, 18.5

[56] References Cited

U.S. PATENT DOCUMENTS

| | | | |
|---|---|---|---|
| 5,053,395 | 10/1991 | Nishio et al. | 536/18.1 |
| 5,091,415 | 2/1992 | Sawada et al. | 514/569 |
| 5,109,122 | 4/1992 | Takeuchi et al. | 536/6.4 |
| 5,194,371 | 3/1993 | Furumai et al. | 536/6.4 |
| 5,227,370 | 7/1993 | Kamachi et al. | 536/6.4 |
| 5,278,052 | 1/1994 | Takeuchi et al. | 536/18.1 |

FOREIGN PATENT DOCUMENTS

0479175A1 9/1991 European Pat. Off. .

OTHER PUBLICATIONS

Y., Sawada et al., "Pradimicins M, N, O and P, New Diydrobenzonaphthacenequinones Produced by Blocked Mutatns of Actinomadura Hibisca P157-2", The Journal of Antibiotics, vol. 46, No. 11, pp. 1367-1374, Nov. 1, 1990.

S. Okuyama et al., "Synthesis and Antifungal Activities of Alanine-Exchanged Analogs of Pradimicin A", The Journal of Antibiotics, vol. 46, No. 3, pp. 500-506, Mar. 1, 1993.

S. Okuyama et al., "Synthesis of 4'-N-Cbz-Pradimic Acid From Pradimicin A", Chemical and Pharmaceutical Bulletin, vol. 41, No. 1, pp. 223-225, Jan. 1, 1993.

D. Ikeda et al., "Amino Acid Analogs of Benanomicin A Through Desalaninebananomicin A", The Journal of Antibiotics, vol. 45, No. 10, pp 1645-1652, Oct. 1, 1992.

*Primary Examiner*—Herbert J. Lilling
*Attorney, Agent, or Firm*—Thomas R. Savitsky

[57] ABSTRACT

The present invention relates to intermediates, pradimic acids and pradimic acid amides of the formula (II)

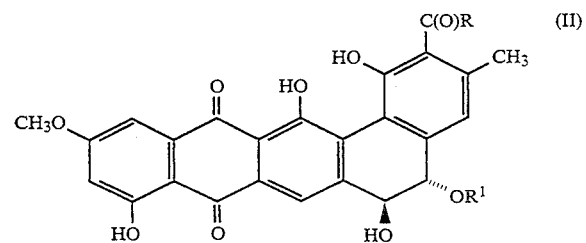

wherein R is OH or $NH_2$; $R^1$ is hydrogen or a group of the formula

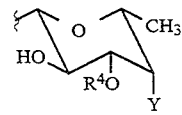

with the proviso that when R is OH, $R^1$ is not hydrogen; Y is OH or $NR^2R^3$; $R^2$ is hydrogen or methyl; $R^3$ is hydrogen, $C_{1-5}$ alkyl, or an amino protecting group; $R^4$ is hydrogen, hydroxy protecting group, or β-D-xylosyl. The invention relates also to novel processes for the preparation of pradimic acids and pradimic acid amides, as well as novel pradimicin derivatives prepared therefrom.

3 Claims, No Drawings

PRADIMIC ACIDS, AMIDES, AND NOVEL PRADIMICIN DERIVATIVES

CROSS REFERENCE TO RELATED APPLICATIONS

This application is a continuation of U.S. patent application Ser. No. 08/214,909 filed Mar. 17, 1994 now abandoned; which is a divisional of U.S. patent application Ser. No. 07/914,908, filed Jul. 16, 1992, now U.S. Pat. No. 5,326,867.

BACKGROUND OF THE INVENTION

1. Field of the Invention

The present invention relates to novel compounds useful as intermediates in the synthesis of pradimicin antibiotics, to processes for preparing these novel intermediates, and to novel pradimicin antibiotics.

2. Background Art

Pradimicins, formerly called BU-3608 antibiotics, are a family of broad spectrum antibiotics active against pathogenic yeasts and fungi. A number of pradimicin compounds obtained by fermentation of *Actinomadura hibisca* have been reported, and their structures are shown below as formula (I):

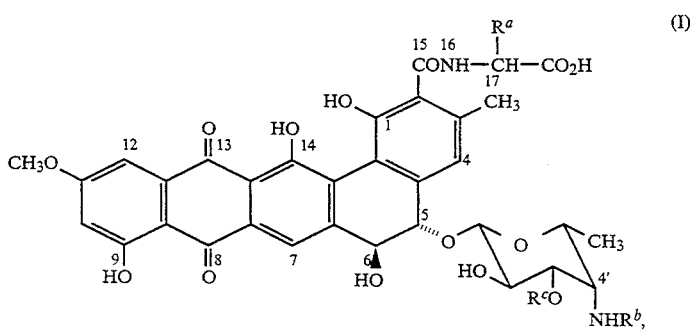

| Pradimicin | $R^a$ | $R^b$ | $R^c$ |
|---|---|---|---|
| A | $CH_3$ | $CH_3$ | β-D-Xylosyl |
| B | $CH_3$ | $CH_3$ | H |
| C | $CH_3$ | H | β-D-Xylosyl |
| D | H | $CH_3$ | β-D-Xylosyl |
| E | H | H | β-D-Xylosyl |
| FA-1 | $CH_2OH$ | $CH_3$ | β-D-Xylosyl |
| FA-2 | $CH_2OH$ | H | β-D-Xylosyl |

U.S. Pat. No. 4,870,165 discloses pradimicins A, B, and C. Pradimicin C is identical to benanomicin B disclosed in European Patent Application No. 315,147 (published May 10, 1989). Benanomicin B, upon vigorous acid hydrolysis, afforded dealanylbenanomicinone (T. Takeuchi et al, *J. Antibiot.*, 1988, 41:707-11).

U.S. Pat. No. 4,992,425 discloses pradimicins D, E, and their respective desxylosyl derivatives.

U.S. Pat. No. 4,960,755 discloses N-alkylated derivatives of pradimicins A, B, C, D, and E.

U.S. Pat. No. 4,973,673 discloses pradimicins FA-1, FA-2, their respective desxylosyl derivatives, and N-alkylated derivatives thereof.

SUMMARY OF THE INVENTION

The present invention provides compounds of the formula (II)

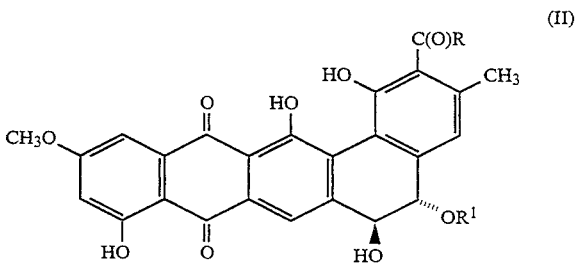

wherein R is OH or $NH_2$; $R^1$ is hydrogen or a group of the formula

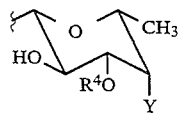

with the proviso that when R is OH, $R^1$ is not hydrogen; Y is OH or $NR^2R^3$; $R^2$ is hydrogen or methyl; $R^3$ is hydrogen, $C_{1-5}$ alkyl, or an amino protecting group; $R^4$ is hydrogen, hydroxy protecting group, or β-D-xylosyl (this sugar fragment with Y and $R^4$ as above defined is sometimes referred to in the specification as the sugar moiety). Compounds of formula (II) are useful as intermediates for pradimicin type antibiotics.

In another aspect of the present invention, there is provided novel pradimicin antibiotics having the formula (VI)

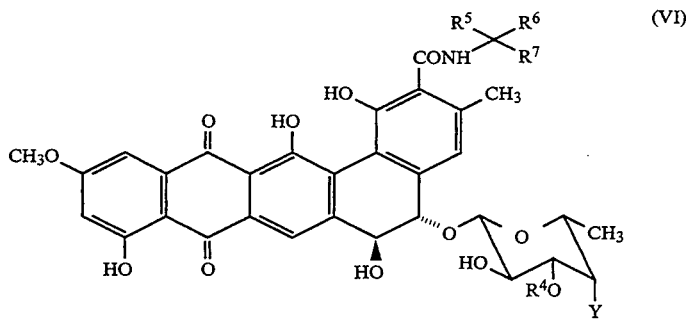
(VI)

wherein Y is OH or $NR^2R^3$; $R^2$ is hydrogen or methyl, and $R^3$ is hydrogen, $C_{1-5}$ alkyl, or an amino protecting group; and $R^4$ is hydrogen, β-D-xylosyl, or a hydroxy protecting group; $R^5$ is hydrogen, $R^7$ is carboxy, $R^6$ is trifluoromethyl, benzyl, aminomethyl, 4-aminobutyl, 3-guanidinylpropyl, ethylcarbamoylthiomethyl, 1-hydroxyethyl, fluoromethyl, 2-amino-2-carboxyethyldithiomethyl, carboxymethyl, or 4-imidazolylmethyl, with the proviso that the amino acid moiety has the D-configuration, or $R^6$ is hydroxymethyl with the proviso that the amino acid has the L-configuration; or $R^5$ and $R^6$ are both hydrogen and $R^7$ is 5-tetrazolyl; or a pharmaceutically acceptable salt thereof.

The present invention also provides a process for the preparation of a compound having the formula

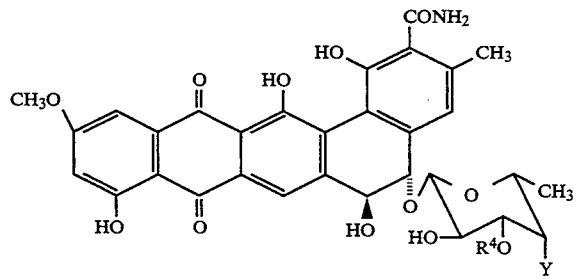

wherein Y is OH or $NR^2R^3$; $R^2$ is hydrogen or methyl; $R^3$ is hydrogen, $C_{1-5}$ alkyl, or an amino protecting group; $R^4$ is hydrogen, hydroxy protecting group, or β-D-xylosyl; which comprises (a) treating a compound having the formula

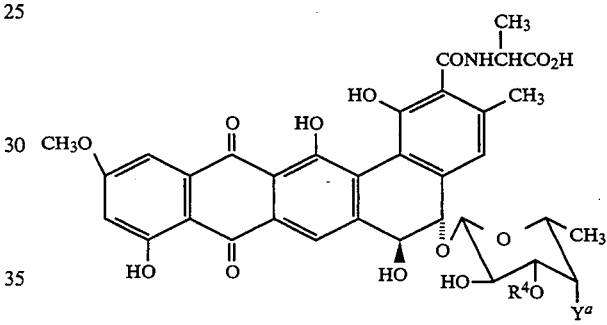

wherein $y^a$ is OH or $NR^{2a}R^{3a}$; $R^{2a}$ is hydrogen or methyl, $R^{3a}$ is $C_{1-5}$ alkyl or an amino protecting group with the proviso that when $R^{2a}$ is hydrogen $R^{3a}$ is an amino protecting group; and $R^4$ is hydrogen, β-D-xylosyl or a hydroxy protecting group; with diphenylphosphoryl azide in the presence of a base; (b) treating the product formed in step (a) with alkaline aqueous alcohol; (c) hydrolyzing the product formed in step (b) under acidic conditions; and (d) optionally replacing the protecting groups with hydrogen.

Another aspect of the present invention provides a process for the preparation of a compound having the formula

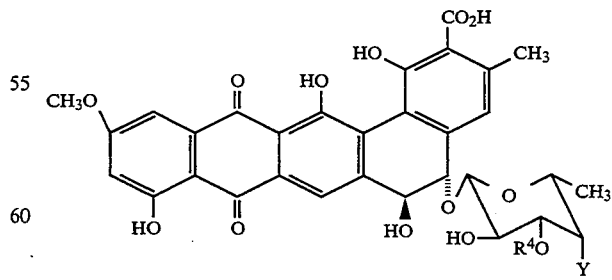

wherein Y is OH or $NR^2R^3$; $R^2$ is hydrogen or methyl; $R^3$ is hydrogen, $C_{1-5}$ alkyl, or an amino protecting group; $R^4$ is hydrogen, hydroxy protecting group, or β-D-xylosyl; which comprises (a) treating a compound of the formula

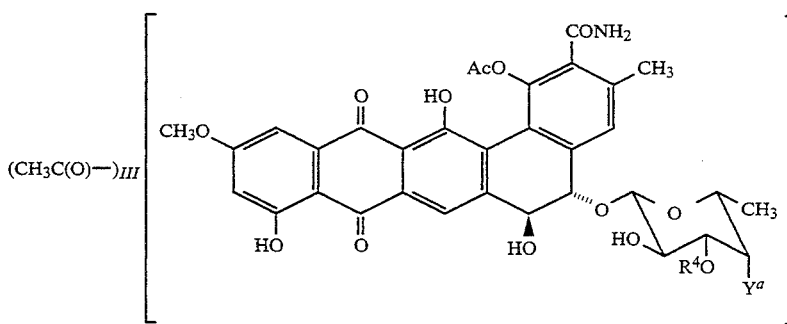

wherein $Y^a$ is OH or $NR^{2a}R^{3a}$; $R^{2a}$ is hydrogen or methyl, $R^{3a}$ is $C_{1-5}$ alkyl or an amino protecting group with the proviso that when $R^{2a}$ is hydrogen $R^{3a}$ is an amino protecting group; and $R^4$ is hydrogen, β-D-xylosyl, or a hydroxy protecting group, m is an integer from 1 to 6, Ac is acetyl; with a compound selected from the group consisting of nitrosonium tetrafluoroborate, nitrosyl chloride, butyl nitrite, sodium nitrite, and nitrogen tetraoxide; (b) removing the acetyl groups; and (c) optionally replacing the protecting groups with hydrogen.

DETAILED DESCRIPTION OF THE INVENTION

In the application, unless otherwise indicated explicitly or by context, the term "alkyl" includes straight or branched saturated carbon chains including methyl, ethyl, propyl, isopropyl, n-butyl, sec-butyl, t-butyl, and pentyl. "Pradimic acid" refers to a compound of formula (II) in which R is OH and $R^1$ is a sugar moiety in which Y and $R^4$ are as defined under formula (II). "Pradimic acid amide" refers to a compound of formula (II) in which R is $NH_2$ and $R^1$ is a sugar moiety in which Y and $R^4$ are as defined under formula (II). "Pradimic acid amide aglycone" refers to the compound of formula (II) in which R is $NH_2$ and $R^1$ is hydrogen.

"Amino protecting group" may be any conventionally used to block an amino group. Examples of amino protecting group include carbamates $R^a$—O—CO wherein $R^a$ may be (but is not limited to) methyl, cyclopropylmethyl, diisopropylmethyl, 9-fluorenylmethyl, t-butyl, t-amyl, 2,2,2-trichloroethyl, 2-iodoethyl, 2-trimethylsilylethyl, isobutyl, 1-methyl-1-phenylethyl, 1,1-dimethyl-2-chloroethyl, cyclobutyl, cyclopentyl, cyclohexyl, 1-methylcyclohexyl, 1-adamantyl, isobornyl, vinyl, allyl, cinnamyl, phenyl, 2,4,6-t-butylphenyl, m-nitrophenyl, 8-quinolyl, benzyl, 2,4,6-trimethylbenzyl, p-methoxybenzyl, 3,5-dimethoxybenzyl, p-nitrobenzyl, o-nitrobenzyl, p-bromobenzyl, diphenylmethyl, p-cyanobenzyl, and 5-benzisoxazolylmethyl; amides $R^b$—CO— wherein $R^b$ may be (but is not limited to) hydrogen, methyl, chloromethyl, trifluoromethyl, o-nitrophenoxymethyl, o-nitrophenylmethyl, phenyl, p-methoxyphenyl, o-nitrophenyl and chloropropyl; benzyl, o-nitrobenzyl, 3,4-dimethoxybenzyl, and triphenylmethyl; trialkylsilyl such as trimethylsilyl and dimethyl-t-butylsilyl.

"Hydroxy protecting group" may be any conventionally used to block a hydroxy group. Examples of hydroxy protecting group include carbonates $R^c$—O—CO— wherein $R^c$ may be (but is not limited to) methyl, ethyl, 2,2,2-trichloroethyl, isobutyl, vinyl, allyl, cinnamyl, p-nitrophenyl, benzyl, 3,4-dimethoxybenzyl, p-methoxybenzyl, o-nitrobenzyl and p-nitrobenzyl; esters $R^d$—CO— wherein $R^d$ may be (but is not limited to) hydrogen, chloromethyl, dichloromethyl, trichloromethyl, trifluoromethyl, methoxymethyl, triphenylmethoxymethyl, phenoxymethyl, p-chlorophenoxymethyl, phenyl, 2,4,6-trimethylphenyl, o-methoxycarbonylphenyl; triorganosilyl, for example, trimethylsilyl, triethylsilyl, isopropyldimethylsily, t-butyldimethylsilyl, (triphenylmethyl)dimethylsilyl, t-butyldiphenylsilyl, methyldiisopropylsilyl and triphenylsilyl; and ethers $R^e$ wherein $R^e$ may be (but is not limited to) methoxymethyl, tetrahydropyranyl, tetrahydrofuranyl, benzyloxymethyl, t-butoxymethyl, 2-methoxyethoxymethyl, 2,2,2-trichloroethoxymethyl, ethoxyethyl, 2,2,2-trichloroethyl, t-butyl, allyl, P-chlorophenyl, benzyl, p-methoxybenzyl, o-nitrobenzyl, p-nitrobenzyl, p-chlorobenzyl, p-cyanobenzyl, diphenylmethyl, and triphenylmethyl.

Additional examples of amino and hydroxy protecting groups may be found in standard reference books such as Greene, *Protective Groups in Organic Synthesis* (John Wiley & Sons, 1981) and McOmie, *Protective Groups in Organic Chemistry*, (Plenum Press, 1973). Selection of a suitable protecting group and methods for introducing and removing the same are within the skills of an ordinary practitioner in organic synthesis; these methods are taught in the textbooks referred to above.

One aspect of the present invention provides compounds of formula (II) which are useful as intermediates in the synthesis of antibiotics of the pradimicin family. Compounds of formula (II) encompasses, where appropriate, their acid addition salts and alkali metal salts. The acid addition salt may be formed with a mineral acid such as hydrochloric acid, hydrobromic acid, sulfuric acid, phosphoric acid, and nitric acid; or with an organic acid such as formic, acetic, propionic, benzoic, fumaric, maleic, tartaric, succinic, oxalic, methanesulfonic, and mandelic acids. Alkali metal salts are for example sodium, potassium, lithium salts, and the like.

In one embodiment of compounds of formula (II), R is: $NH_2$ and $R^1$ is hydrogen or a group of the formula

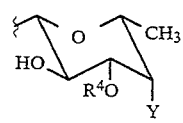

wherein Y is OH or $NR^2R^3$; $R^2$ is hydrogen or methyl; $R^3$ is hydrogen, $C_{1-5}$ alkyl, or an amino-protecting group; and $R^4$ is hydrogen, β-D-xylosyl, or a hydroxy protecting group. In one preferred embodiment, $R^1$ is hydrogen. In another preferred embodiment, $R^1$ is the group of the formula

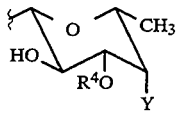

wherein $R^4$ is β-D-xylosyl, Y is OH or $NR^2R^3$; $R^2$ is methyl, and $R^3$ is hydrogen or an amino protecting group; preferred amino protecting groups are benzyloxycarbonyl or t-butoxycarbonyl.

In another embodiment of compounds of formula (II), R is OH and $R^1$ is a group of the formula

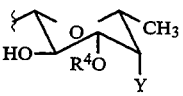

wherein Y is OH or $NR^2R^3$; $R^2$ is hydrogen or methyl; $R^3$ is hydrogen, $C_{1-5}$ alkyl, or an amino protecting group; and $R^4$ is hydrogen, β-D-xylosyl, or a hydroxy protecting group. In a preferred embodiment $R^4$ is β-D-xylosyl, $R^2$ is methyl, and $R^3$ is hydrogen or an amino protecting group; preferred amino protecting groups are benzyloxycarbonyl or t-butoxycarbonyl.

Compounds of formula (II) in which R is $NH_2$ and $R^1$ is a group of the formula

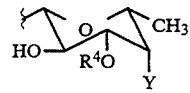

wherein Y and $R^4$ are as defined under formula (II), may be prepared from known pradimicin derivatives by two methods:

The first method involves treating an appropriate pradimicin derivative, such as amino-protected (N-protected) pradimicin A, B or C, or N,O-bis-protected pradimicin B (amino and 3'-hydroxy protected), or 4'-desmethylamino-4'-hydroxypradimicin A or an N-dialkylated pradimicin, with acetic anhydride in pyridine followed by alkaline hydrolysis to give the corresponding desalanyl amide (IIa) and a side product of formula (III). This method is illustrated in Scheme I.

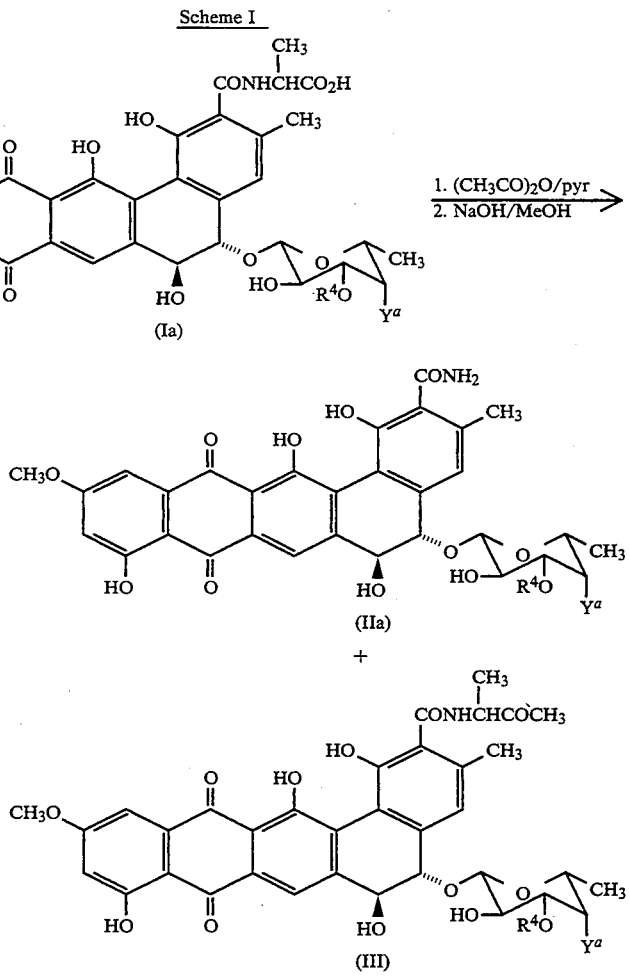

In Scheme I, $Y^a$ is OH or $NR^{2a}R^{3a}$; $R^{3a}$ is $C_{1-5}$alkyl or an amino protecting group, $R^{2a}$ is hydrogen or methyl, with the proviso that when $R^{2a}$ is hydrogen, $R^{3a}$ is an amino protecting group; and $R^4$ is hydrogen, β-D-xylosyl, or a hydroxy protecting group. The conversion of (Ia) to (IIa) may be accomplished by heating (Ia) in acetic anhydride and pyridine followed by alkaline hydrolysis. The reaction is carried out at temperature of about 50 to 120° C, for a period of from about 10 minutes to about 15 hours. The reaction temperature and duration will depend of the reactants and reagents used; for example, in the case of pradimicin A in acetic anhydride/pyridine, the reaction is preferably run at about 120° for about an hour. Alkaline hydrolysis may be effected with, for example, sodium hydroxide in methanol. The product obtained is a mixture of the desired pradimic acid amide (IIa) and the side product (III); separation of the mixture is effected by conventional techniques, e.g. column chromatography.

The second method for converting pradimicin to pradimic acid amide is illustrated in Scheme II.

mixture, to give a diastereomeric mixture of oxazinone (IV).

Although the diastereomeric mixture of oxazinone may be separated into the individual diastereomers, it is not necessary to do so. Thus the diastereomeric mixture is subjected to alkaline hydrolysis, for example with 1N sodium hydroxide and methanol at room temperature to provide a diastereomeric mixture of the corresponding methoxy compounds of formula (v); generally, the reaction is complete within about 10 hours. The individual diastereomers of formula (V), or a mixture thereof, may be easily converted to pradimic acid amide (IIa) by acid

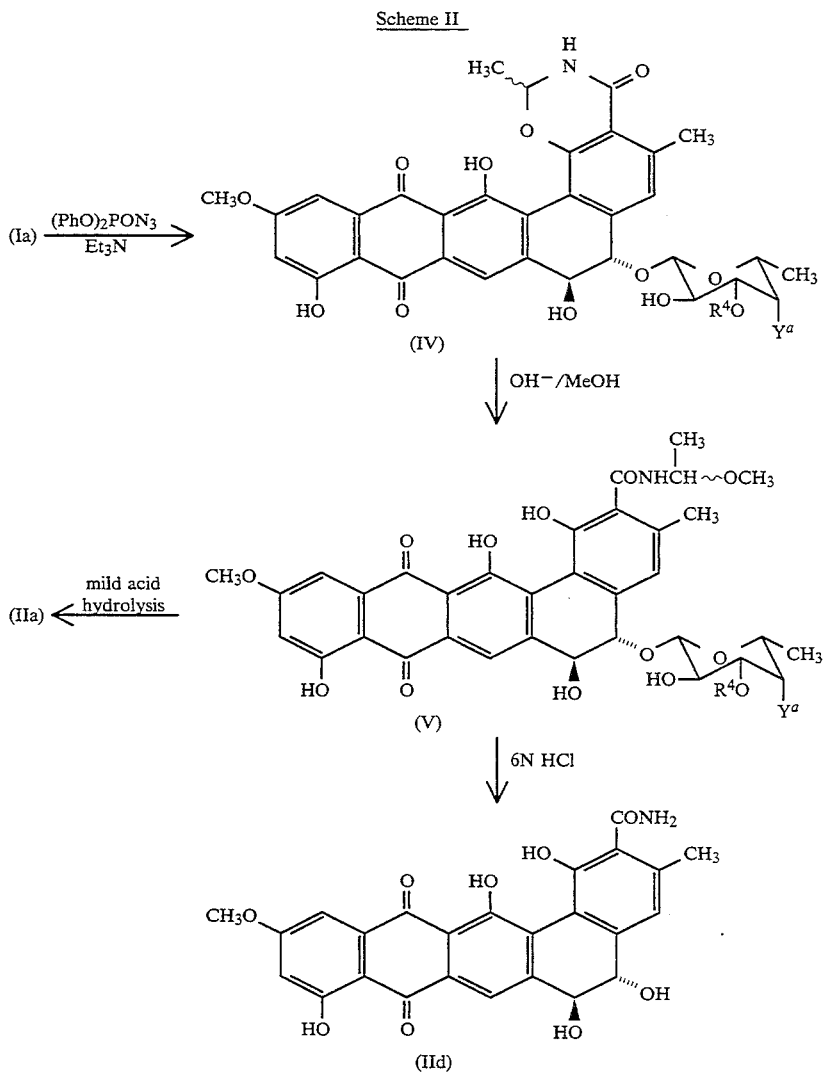

In Scheme II, $Y^a$ and $R^4$ have the same meaning as previously defined in Scheme I. In this process, however, where $R^4$ is hydrogen, the amino protecting group is preferably one other than benzyloxycarbonyl; or where benzyloxycarbonyl is used as the amino protecting group, $R^4$ is preferably not hydrogen. Thus, a pradimicin of formula (Ia) is treated with an azide reagent, for example diphenylphosphoryl azide, in the presence of an organic base, for example a tertiary amine base such as triethylamine, diisopropylethylamine, dimethylaminopyridine, and the like. The reaction is carried out in a solvent such as t-butanol, DMF, dioxane and benzene at an elevated temperature, for example at the refluxing temperature of the reaction hydrolysis; for example the diastereomeric mixture of compounds of formula (V) is treated with 3N HCl in acetonitrile at room temperature for 3 days to provide the desired amide (IIa).

Compounds of formula (V) may also be converted to pradimic acid amide aglycone (IId) under vigorous acid hydrolysis. For example, refluxing a diastereomeric mixture of compounds of formula (V) in 6N HCl and dioxane for five hours gives the desired aglycone amide (IId).

It will be appreciated that by the process depicted in Scheme II compounds of formula (IIa) and pradimic acid amide aglycone may be obtained from the starting-material (Ia) in one reaction sequence without isolating the oxazinone (IV) or methoxy (V) intermediate.

The protecting groups of pradimic acid amides of formula (IIa), when present, may be optionally removed using conventional deprotecting methods. Deprotection method will depend on the nature of the amino protecting group used; examples of deprotecting method are acid or alkaline hydrolysis, catalytic hydrogenolysis, and reduction.

Compounds of formula (II) wherein R is $NH_2$, $R^1$ is the sugar moiety in which Y is $NR^2R^3$; $R^2$ and $R^4$ are as defined under formula (II), and $R^3$ is alkyl may also be prepared from the corresponding compounds of formula (II) wherein $R^3$ is hydrogen by reductive alkylation. The starting pradimic acid amide is reacted with an aldehyde or a ketone to form the corresponding imine which is reduced to give the N-alkylated product.

The carbonyl reactant may be an aldehyde or a ketone having one to five carbon atoms, for example, formaldehyde, acetaldehyde, propionaldehyde, and acetone. Reduction of the imine may be accomplished by using reducing agents such as metal hydrides, for example, sodium borohydride, sodium cyanoborohydride, lithium aluminum hydride. The reaction is carried out in a polar organic solvent or a mixture thereof such as water, acetonitrile, lower alkanols, and dimethyl sulfoxide. The reaction temperature is not particularly restricted and may be from room temperature to about 100° C. In our experience, the alkylation reaction carried out at room temperature is usually complete within 24 hours. Optimum reaction conditions will of course depend on the nature and reactivity of the particular reactants used.

The pradimic acid amides are themselves intermediate compounds that can be used to prepare antifungally active pradimicin derivatives. As an example, a pradimic acid amide, with its reactive hydroxy groups and reactive amino group, if present, protected, is treated with a strong base, such as sodium hydride, to generate the amide anion. Reaction with ethyl iodoacetate followed by deprotection yields the corresponding pradimicin D analog. In a similar manner, pradimic acid amide aglycone can be converted to the aglycone of pradimicin D.

In another embodiment of compounds of formula (II), R is OH and $R^1$ is a group of the formula

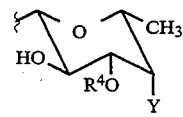

wherein Y is OH or $NR^2R^3$; $R^2$ is hydrogen or methyl; $R^3$ is hydrogen, $C_{1-5}$ alkyl, or an amino protecting group; $R^4$ is hydrogen, hydroxy protecting group, or β-D-xylosyl. These compounds may be prepared from the corresponding pradimic acid amide of formula (IIa) by the process shown in Scheme III.

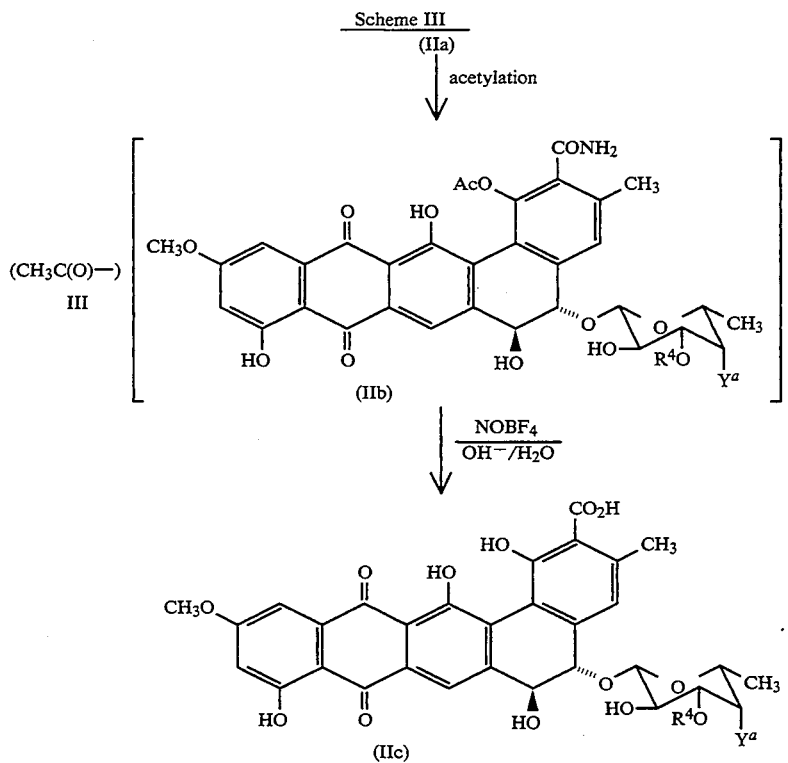

In Scheme III, $Y^a$ and $R^4$ have the same meaning as defined in Scheme I; m is an integer from 1 to 6; and Ac is a lower alkanoyl, e.g., acetyl. In the first step of the process, free accessible hydroxyl groups are blocked by reacting a compound of formula (IIa) with an acylating agent, for example acetic anhydride, acetic acid and dicyclohexylcarbodiimide, or acetyl chloride, in the presence of a tertiary amine base, e.g. pyridine. However, because it is advantageous to have the 1-OH group blocked prior to the subsequent reaction step, the following method, which has been shown to selectively acylate the 1-OH group of pradimicin A methyl ester, is preferably carried out first, where $Y^a$ of the compound of formula (IIa) is $NR^{2a}R^{3a}$.

Pradimic acid amide (IIa) is acylated under phase transfer conditions using an appropriate acylating agent such as an acyl halide. Suitable acyl halides are for example acetyl chloride and propionyl chloride. The reaction is conducted in an inert organic solvent such as methylene chloride, tetrahydrofuran, ether, dioxane and toluene. The reaction mixture includes a base in solid form; suitable bases include sodium hydroxide, potassium hydroxide, sodium bicarbonate, sodium carbonate and the like. The phase transfer catalyst may be for example tetrabutylammonium hydrogen sulfate, tetrabutylammonium dihydrogen phosphate, as well as other reagents that can bring the pradimicin reactant into the same phase as the acylating reagent. The reaction may be carried out at temperature ranging from about −50° C. to about 50° C., but preferably it is carried out at room temperature. The reaction time may range from several minutes to several hours. In a preferred embodiment the acylation is effected in an organic solvent using acetyl chloride in the presence of tetrabutylammonium hydrogen sulfate (TBAH) and powdered sodium hydroxide; the reaction using these reagents generally takes less than one hour to complete at room temperature. Phase transfer catalyzed acylation using TBAH/NaOH/organic solvent is described by Illi, V. O. in Tet. Lett., 1979, 2431-2432. Using the procedure provided herein above, the phenolic hydroxyl group at the 1-position is preferentially acylated over the aliphatic hydroxyl groups and the phenolic hydroxyl groups at the 9- and 14-positions.

The peracylated amide (IIb) is then treated with nitrosonium tetrafluoroborate (NOBF$_4$) to convert the amide into the corresponding peracylated N-protected pradimic acid. The reaction is carried out in an inert organic solvent such as nitromethane,. dichloromethane and acetonitrile; preferably, acetonitrile is used as the reaction solvent; and in the presence of a tertiary amine base, such as triethylamine, dimethylaminopyridine, diisopropylethylamine and the like. The reaction temperature may range from −10° C. to 50° C., and the reaction is usually completed in 30 hours; typically the reaction is conducted at ambient temperature for about 20 hours. Although nitrosonium tetrafluoroborate is the preferred reagent for converting the peracylated amide (IIb) into the corresponding acid, other reagents such as nitrosylchloride, butyl nitrite, and sodium nitrite and dinitrogen tetraoxide can also be used for this purpose.

The hydroxy protecting groups of peracylated N-protected pradimic acid are then removed by alkaline hydrolysis to yield pradimic acid of formula (IIc). The amino protecting group is removed according to procedure previously described to provide compounds of formula (II) in which R is OH and R$^1$ is the sugar moiety in which Y and R$^4$ are as defined under formula (II). The amino group of such compounds may be further alkylated to provide the corresponding pradimic acids in which R$^3$ is an alkyl group by procedure previously provided above.

The pradimic acids (compounds of formula (II) in which R is OH) may be further elaborated to provide novel pradimicin type antifungal agents. Thus, another aspect of the present invention provides novel antifungal compounds having the formula (VI)

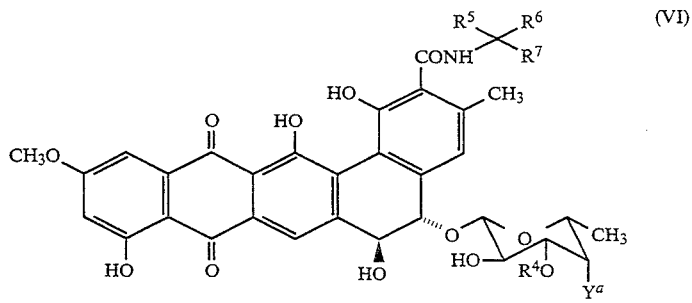

wherein Y is OH or NR$^2$R$^3$; and R$^4$ are as defined under formula (II); R$^5$ is hydrogen, R$^7$ is carboxy, R$^6$ is trifluoromethyl, benzyl, aminomethyl, 4-aminobutyl, 3-guanidinylpropyl, ethylcarbomoylthiomethyl, 1-hydroxyethyl, fluoromethyl, 2-amino-2carboxyethyldithiomethyl, carboxymethyl, or 4-imidazolylmethyl, with the proviso that the amino acid moiety has the D-configuration, or R$^6$ is hydroxy methyl with the proviso that the amino acid moiety has the L-configuration; or R$^5$ and R$^6$ are both hydrogen and R$^F$ is 5-tetrazolyl; or a pharmaceutically acceptable salt thereof.

Compounds of formula (VI) are prepared by reacting a pradimic acid or an acylating equivalent thereof, where necessary with the 4′-amino group protected, with an amine of the formula

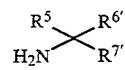

wherein R$^5$ is as defined above, R$^{6'}$ is R$^6$ or a protected R$^6$, and R$^{7'}$ is R$^7$ or a protected R$^7$, using conventional acylation procedures. An acylating equivalent may be for example the corresponding acid chloride, an activated ester such as formed with 1-hydroxybenzotriazole, or an anhydride. The acylation reaction is carried out in an inert organic solvent such as methylene chloride, tetrahydrofuran, and the like, and in the presence of an acid scavenger such as an tertiary organic base, for example, triethylamine, diisopropylethylamine, dimethylaminopyridine and the like. The reaction is conducted at a temperature conducive for product formation, and generally the reaction may be carried out at room temperature. The protecting groups are optionally removed using conventional deprotecting methods to give the various novel pradimicin compounds of formula (VI).

BIOLOGICAL ACTIVITY

Antifungal activities of representative compounds of the present invention were evaluated in vitro. The minimum inhibitory concentrations (MICs) against various fungi were determined by serial agar dilution method using Sabouraud dextrose agar. Thus, approximately 0.003 ml of fungal suspension containing 10$^6$ cells/ml was applied to the surface of agar plates containing the test antibiotics. The MIC values recorded after the cultures had been incubated for 40 hours at 28° C. are set forth below in Table 1.

TABLE 1

In vitro Antifungal Activity of Pradimicin Derivaties
MIC (μg/ml)

| Compound | Candida albicana | Cryptococcus neoformans | Aspergillus fumigatus | Trichophyton mentagrophytes |
| --- | --- | --- | --- | --- |
| Pradimicin A | 12.5 | 3.1 | 1.6 | 3.1 |
| Example 13 | >50.0 | 25 | >50 | 50 |
| Example 14 | 12.5 | 12.5 | >100 | >100 |
| Example 15 | 25 | 6.3 | 6.3 | 6.3 |
| Example 16 | 12.5 | 6.3 | 50 | 12.5 |
| Example 17 | >100 | 3.1 | 50 | >100 |
| Example 18 | >100 | 1.6 | 6.3 | 12.5 |
| Example 19 | >50 | 12.5 | 50 | 12.5 |
| Example 20 | 6.3 | 3.1 | 3.1 | 3.1 |
| Example 21 | 25 | 6.3 | 6.3 | 6.3 |
| Example 22 | >100 | 6.3 | 3.1 | 12.5 |
| Example 23 | 25 | 3.1 | 3.1 | 12.5 |
| Example 27 | 12.5 | 6.3 | 12.5 | 12.5 |
| Example 28 | 6.3 | 3.1 | 6.3 | 6.3 |
| Example 29 | 6.3 | 3.1 | 6.3 | 12.5 |
| Example 30 | 12.5 | 50 | >100 | >100 |
| Example 31 | 6.3 | 3.1 | 3.1 | 3.1 |

For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preparations for parenteral administration include sterile aqueous or non-aqueous solutions, suspensions, or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that, when treating a host infected with a fungus susceptible to the antibiotics of this invention, the actual preferred route of administration and dosage used will be at the discretion of the attending clinician skilled in the treatment of fungal infections and will vary according to the causative organism, its sensitivity to the antibiotic, severity and site of the infection, and patient characteristics, such as age, body Weight, rate of excretion, concurrent medications, and general physical condition.

The following examples are provided in order to more fully illustrate the present invention; they are not intended to limit the scope of the invention in any manner. In the examples, the terms pradimic acid and pradimic acid amide refer to the acid and amide derived from pradimicin A.

EXAMPLE 1

Preparation of 4'-N-(benzyloxycarbonyl)-Pradimic Acid Amide (CBZ=benzyloxycarbonyl) (Method I)

(a) preparation of 4'-N-CBZ-pradimicin A (1)

To a mixture of pradimicin A hydrochloride (4.1 g, 4.7 mmol) and N,O-bis(trimethylsilyl)acetamide (BSA, 30 ml, 121 mmol) in $CH_2Cl_2$ (160 ml) was added benzyl chloroformate (6.5 ml, 46 mmol). The mixture was stirred for 3 hr at room temperature and then concentrated in vacuo. To the residue was added MeOH (160 ml) and 1N HCl (120 ml). The mixture was stirred for 30 min, and MeOH was removed in vacuo. To the residue was added $H_2O$ and the precipitate formed was collected by filtration, and washed with $H_2$. The solid was dissolved in MeOH (50 ml) and isopropyl ether was added to precipitate 4.4 g (Yield, 96%) of 1 as a red amorphous powder. MP 195°–200° C. (dec).

IR $\nu_{max}$ (KBr) $CM^{-1}$ 1720, 1660, 1620, 1600 UV $\lambda_{max}$ (1/100N NaOH) nm (ε) 498 (12700), 320 (12700). MS (FAB) m/z 975 $(M+H)^+$. $^1H$ NMR (DMSO-$d_6$) δ1.01 (3H, d, J=6 Hz), 1.33 (3H, d, J=7 Hz), 2.28 (1.5H, s), 2.29 (1.5H, s) 3.58 (0.5H, dd, J=6 & 11 Hz), 3.63 (0.5H, dd, J=6 & 11 Hz), 3.95 (3H, s), 4.39 (1H, qui, J=7 Hz), 4.67 (1H, br), 5.01 (1H, ABg, J=13 Hz), 5.11 (1H, ABg, J=13 Hz), 6.94 (1H, d, J=3 Hz), 7.07 (1H, s) 7.30 (1H, d, J=3 Hz), 7.34–7.39 (5H, m), 8.06 (1H, s), 8.56 (1H, d, J=7 Hz).

(b) preparation of 4'N-CBZ-pradimic acid amide (2)

To a solution of 1 (250 mg, 0.26 mmol) in pyridine (2 ml) was added acetic anhydride (1 ml) and the mixture was immediately heated at 120° C. for 1 hr. The reaction mixture was concentrated under reduced pressure. The residue (303 mg) was dissolved in a solution of MeOH (3 ml) and 1N NaOH (3 ml), and allowed to stand Overnight at room temperature. The reaction mixture was adjusted to pH 2 with 1N HCl and the resulting precipitate was filtered off and dried to give a solid (220 mg). Preparative HPLC using 48% $CH_3CN$-pH 3.5 buffer as eluant gave mainly two homogeneous fractions. The first eluted fraction was concentrated under reduced pressure, and the residue desalted on a HP-20 column using water and 80% acetone as eluant. Removal of acetone from the eluate gave precipitate of 2, which was collected by filtration (56 mg, yield 24%). The second eluted fraction was similarly treated to provide 4'-N-CBZ-17-(RS)-acetyl-17-descarboxypradimicin A (3, 78 mg, yield 31%).

2 MP 212°–220° C. (dec). IR $\nu_{max}$ (KBr) $cm^{-1}$ 1660, 1600. UV $\lambda_{max}$ (50% MeOH-1/100N NaOH) nm (λ) 498 (10300), 320 (9400), 248 (17700). MS (FAB) m/z 903 $(M+H)^{30}$ $^1H$ NMR (DMSO-$d_6$) δ1.02 (3H, d, J=6 H/z), 2.31 (1.5H, s), 2.32 (1.5 H, s), 3.58 (0.5H, dd, J=5 & 11 Hz), 3.62 (0.5H, dd, J=5 & 11 Hz), 3.96 (3H, s), 4.66 (1H, br), 5.01 (1H, ABq, J=13 Hz), 5.10 (1H, ABq, J=13 Hz), 6.94 (1H, d, J=2 Hz), 7.06 (1H, s), 730 (1H, d, J=2 Hz), 7.34–7.39 (5H, m), 7.54 (1H, br), 7.66 (1H, br), 8.05 (1H, s).

EXAMPLE 2

Preparation of 4'-N-CBZ-pradimic acid amide (Method II)

(a) preparation of 4'-N-CBZ-pradimicin oxazinones (4)

A mixture of 1 (200 mg, 0.21 mmol), $Et_3N$ (68 mg, 0.67 mmol) and diphenylphosphoryl azide (216 mg, 0.78 mmol) in t-BuOH (10 ml) was heated under reflux for 3 days under argon atmosphere. The cooled reaction mixture was extracted with EtOAc (100 ml), washed with water (100 ml×3) and brine (50 ml), dried over anhydrous $MgSO_4$, and concentrated under reduced pressure. The crude mixture was chromatographed on a column of Bondapack C-18, which was eluted with 50% $CH_3CH$—$H_2O$. The desired fractions were combined and concentrated to give (4-isomer A) (107 mg, Yield 56%) and (4-isomer B) (53 mg, Yield 27%). HPLC; Column SSC-ODS-262, Flow rate 1 ml/min, Mobile phase acetonitrile-pH 3.5 phosphate buffer 55:45, Retention time: 4-isomer A 5.5 min; 4-isomer B 8.8 min.

4-isomer A: MP 230°–240° C. (dec). IR $\nu_{max}$ (KBr) cm$^{-1}$ 1665, 1600. UV $\lambda_{max}$ (MeOH) nm ($\epsilon$) 242 (28900), 286 (20800), 458 (10400). MS (FAB) m/z 929 (M+H)$^{30}$, $^1$H NMR (DMSO-d$_6$) $\delta$1.04 (3H, d, J=6 Hz), 1.42 (3H, d, J=6 Hz), 2.64 (3H, s), 3.5–3.7 (1.H, m), 3.96 (3H, s), 5.01 (1H, ABq, J=13 Hz), 5.11 (1H, ABq; J=13 Hz), 6.94 (1H, d, J=3 Hz), 7.29 (1H, s), 7.30 (1H, d, J=3 Hz), 7.3–7.4 (5H, m), 8.05 (1H, s), 8.81 (1H, br). 4-isomer B: MP 220°–225° C. (dec). IR $\nu_{max}$(KBr) cm$^{-1}$ 1665, 1600. UV $\lambda_{max}$ (MeOH) nm ($\epsilon$) 242 (19500), 286 (14200), 456 (7600). MS (FAB) m/z 929 (M+H)$^+$. $^1$H NMR (DMSO-d$_6$) $\delta$1.03 (3H, d, J=6 Hz), 1.45 (3H, d J=6 Hz), 2.64 (1.5H, s), 2.65 (1.5H, s), 3.96 (3H, s), 5.02 (1H, ABq, J=12 Hz), 5.12 (1H, ABq, J=12 Hz), 5.52 (1H, br), 6.94 (1H, d, J=3 Hz), 7.30 (1H, d, J=3 Hz), 7.3–7.4 (5H, m), 8.06 (1H, s), 8.72 (1H, br).

(b) preparation of 4'-N-CBZ-17-descarboxy-17-methoxy pradimicin A (5)

The oxazinone derivative (4-isomer B) (30 mg, 0.032 mmol) was dissolved in MeOH (3 ml) and 1N NaOH (0.3 ml) and the mixture was stirred for 4 hr at room temperature. The mixture was neutralized with 1N HCl to pH 6-7 and MeOH was removed in vacuo. The residue was extracted with EtOAc (100 ml), washed with brine, dried over Na$_2$SO$_4$ and concentrated. The residue was triturated with ether to give 28 mg (Yield 90%) of the title compound (5).

The oxazinone derivative (4-isomer A) (41 mg, 0.044 mmol) was treated as described above to give 40 mg (Yield 94%) of the methoxy derivative (5). HPLC; Column SSC-ODA-262, Flow rate 1 ml/min, Mobile phase acetonitrile-pH 3.5 phosphate buffer 50:50, Retention time 5 10.0 min.

$^1$H NMR (DMSO-d$_6$) $\delta$1.03 (3H, d, J=6 Hz), 1.28 (3H, d, J=6 Hz), 2.25 (3H, s), 3.58 (0.5H, dd, J=5 & 11 Hz), 3.63 (0.5H, dd, J=5 & 11 Hz), 3.96 (3H, s), 4.67 (1H, br), 5.02 (1H, ABq, J=13 Hz), 5.11 (1H, ABq, J=13 Hz), 5.28 (1H, m), 6.95 (1H, d, J=2 Hz), 7.08 (1H, s), 7.30 (1H, d, J=2 Hz), 7.3–7.4 (5H, m), 8.01 (1H, s), 8.59 (1H, d, J=9 Hz).

(c) preparation of 4'-N-CBZ-pradimic acid amide (2)

A mixture of 5 (130 mg, 0.14 mmol) was dissolved in a mixture of 3N HCl (20 ml) and CH$_3$CN (40 ml) and the mixture was stirred for 3 days at room temperature. After CH$_3$CN was removed in vacuo, the residue was chromatographed on a column of C-18 silica gel (Bondapak C$_{18}$, Waters, 40 i.d.×300 mm) eluted with 45–50% CH$_3$CN-pH 3.5 buffer. The desired fractions were combined and concentrated. The precipitate formed was collected by filtration, washed with water, and dried to give 37 mg (Yield, 29%) of 2.

EXAMPLE 3

Preparation of 4'-N-CBZ-Pradimic Acid Amide (2) according to method II without isolating the intermediates.

A mixture of 1 (185 mg, 0.19 mmol), NEt$_3$ (60 mg, 0.59 mmol) and diphenylphosphoryl azide (162 mg, 0.59 mmol) in t-BuOH (10 ml) was heated under reflux for 4 hr under argon atmosphere. After concentration, 1.0% citric acid (10 ml) was added and the mixture was extracted with EtOAc. The insoluble materials were collected by filtration and added to the organic layer. EtOAc was removed in vacuo, and the residue containing oxazinone 4 was dissolved in MeOH-1N NaOH (1:1, 20 ml). The mixture was stirred overnight at room temperature and MeOH was removed in vacuo. The residue was treated with 3N HCl (20 ml) and CH$_3$CN (30 ml) overnight. After evaporation of CH$_3$CN, the precipitated crude product was collected by filtration and chromatographed on a column of C-18 silica gel (Bondapak C$_{18}$, 40 i.d.×300 mm). The column was eluted with CH$_3$CN-pH 3.5 buffer (45:55) and the desired fractions were combined. After concentration, the precipitated product was collected by filtration, washed with H$_2$O and dried over P$_2$O$_5$ to give 121 mg (Yield 71%) of 2.

EXAMPLE 4

Preparation of Pradimic Acid Amide (6)

To a mixture of 2 (26 mg), MeOH (2 ml), water (0.5 ml) and acetic acid (0.5 ml) was added 10% Pd on carbon (10 mg) and the mixture was subjected to hydrogenation at room temperature for 5 hours. The reaction mixture was filtered and washed with acetic acid. The filtrate was concentrated in vacuo and chromatographed on a column of Bondapak C-18. The column was eluted with 40% acetonitrile-pH 3.5 buffer. The fractions containing the product were combined and concentrated. The concentrate was desalted chromatographically by using HP-20 column to give 18 mg (81%) of the title compound. MP 186°–189° C. (dec).

IR $\nu_{max}$ (KBr) cm$^{-1}$ 3339, 1656, 1607. UV $\lambda_{max}$ (1/100N NaOH) nm ($\epsilon$) 250 (34600), 315 (16600) 495 (10700). MS (SIMS) 769 [M+H]$^+$. $^1$H NMR (DMSO-d$_6$) $\delta$1.24 (3H, d, J=6.5 Hz), 2.27 (3H, s), 3.73 (1H, dd, J=5.2 & 11.2), 3.85 (1H, m), 3.90 (3H, s), 4.44 (1H, d, J=10.5 Hz), 4.45 (1H, d, J=7.3 Hz), 4.46 (1H, d, J=10.5 Hz), 4.72 (1H, d, J=7.3 Hz), 6.69 (1H, d, J=2.5 Hz), 6.86 (1H, s), 7.12 (1H, d, J=2.5 Hz), 7.62 (1H; s).

EXAMPLE 5

Preparation of Pradimic Acid Amide Aglycone (7).

A mixture of 4 (0.90 g, 0.97 mmol) in MeOH (100 ml) and 1N NaOH (10 ml) was stirred for 4 hr at room temperature and evaporated under reduced pressure. To the residue was added dioxane (40 ml) and 6N HCl (40 ml) and the mixture was heated under reflux for 5 hr. After concentration in vacuo, the residue was chromatographed on a column of HP-20 (50 i.d.×200 mm). The column was eluted with water and then 80% MeCN. The fraction containing the desired product was concentrated in vacuo to give 340 mg of the crude material. The material was dissolved in 1/100N NaOH and chromatographed on a column of C$_{18}$ silica gel (Bondapak C$_{18}$, Waters, 30 i.d.×250 mm). Elution with 5–10% MeCN in water afforded fractions containing the desired product, which were combined and concentrated in vacuo. The aqueous residue was acidified with HCl and the resulting precipitate was collected to give 224 mg (yield 48%) of the title product. Analytical sample was crystallized from DMSO, as deep orange needles, M.P. >300° C.

Anal Calcd for C$_{25}$H$_{19}$NO$_9$ 1/2H$_2$O: C 61.73, H 4.14, N 2.88. Found: C 61.63, H 3.93, N 2.89.

IR $\nu_{max}$ (KBr) cm$^{-1}$ 1650, 1600. UV $\lambda_{max}$ (1/100N NaOH) nm ($\epsilon$) 249 (30000), 319 (15000), 495 (13400). MS (FAB) m/z 478 (M+H)$^+$. $^1$H NMR (DMSO-d$_6$) $\delta$2.30 (3H, s), 3.89 (3H, s), 4.20 (2H, s), 6.74 (1H, d, J=2

Hz), 6.92 (1H, s), 7.14 (1H, d, J=2 Hz), 7.23 (1H, br), 7.55 (1H, br), 7.84 (1H, s).

EXAMPLE 6

Preparation of 4'-N-t-butoxycarbonyl-Pradimic Acid Amide (t-BOC=t-butoxycarbonyl)

(a) preparation of 4'-N-t-BOC pradimicin A (8)

Di-t-butyl dicarbonate (750 mg, 3.44 mmol) was added to a mixture of pradimicin A hydrochloride (300 mg, 0.342 mmol) and BSA (1.7 ml, 6.88 mmol) in $CH_2Cl_2$ (9 ml) and the mixture was stirred overnight at room temperature. Tetrabutylammonium fluoride (1M in THF, 6.9 ml) was added and the mixture was stirred for 30 min. The mixture was acidified to pH 4–5 with 0.1N HCl and diluted with water. The precipitate formed was collected by filtration, washed with water and dried. The precipitates were dissolved in a small amount of MeOH and the mixture was diluted with isopropyl ether to precipitate 224 mg (70%) of 8. MP 195°–205° C. (dec).

IR $v_{max}$ (KBr) cm$^{-1}$ 1720, 1660, 1620, 1600. UV $\lambda_{max}$ (1/100N NaOH) nm ($\epsilon$) 322 (10000), 499 (11600). $^1$H NMR (DMSO-d$_6$) $\delta$1.01 (1H, d, J=6 Hz), 1.03 (2H, d, J=6 Hz), 1.34 (3H, d, J=7 Hz), 1.37 (6H, s), 1.40 (3H, s), 2.29 (3H, s), 3.67 1H, dd, J=6 & 12 Hz), 3.94 (3H, s), 4.39 (1H, qui, J=7 Hz), 4.65 (1H, d, J=7 Hz), 6.85 (1H, br), 6.96 (1H, s) 7.23 (1H, br), 7.93 (1H, br), 8.68 (1H, d, J=7 Hz). Ms (FAB) m/z 941 (M+H)$^{30}$.

(b) preparation of 4'-N-t-BOC-pradimicin oxazinones (9)

The general procedure described in example 2 (a) was repeated using (8) (15 mg, 0.016 mmol), Et$_3$N (2 mg, 0.020 mmol) and diphenylphosphoryl azide (6 mg, 0.022 mmol) in t-BuOH (0.5 ml). Chromatography on Bondapack C-18 column using 65% CH$_3$CN—H$_2$O as eluent provided 9-isomer A (2.1 mg, 15%) and 9-isomer B (4.0 mg, 28%). Retention time 9-isomer A 5.7 min; 9-isomer B 9.2 min.

9 isomer-A: MP 185°–195° C. (dec). IR $v_{max}$ (KBr) cm$^{-1}$ 1680, 1630, 1610. UV $\lambda_{max}$ (MeOH) nm ($\epsilon$) 242 (26900), 286 (19600), 456 (10600). MS (FAB) m/z 895 (M+H)$^+$. $^1$H NMR (DMSO-d$_6$) $\delta$1.02 (1H, d, J=7 Hz), 1.04 (2H, d, J=7 Hz), 1.37 (6H, s), 1.41 (3H, s), 2.63 (3H, s), 3.96 (3H, s), 6.95 (1H, d, J=3 Hz), 7.32 (1H, d, J=3 Hz), 8.06 (1H, s), 8.81 (1H, br).

9 isomer-B: MP >220° C. (dec). IR $v_{max}$(KBr) cm$^{-1}$ 1680–1670, 1610. UV $\lambda_{max}$ (MeOH) nm ($\epsilon$) 242 (26800), 286 (20100), 455 (10200). MS (FAB) m/z 917 (M+Na)$^+$. $^1$H NMR (DMSO-d$_6$) $\delta$1.02 (1H, d, J=6 Hz), 1.04 (2 Hz, d, J=6 Hz), 1.37 (6H, s), 1.41 (3H, s), 1.45 (3H, d, J=6 Hz), 2.65 (3H, s), 3.68 (1H, dd, J=6 & 11 Hz), 3.95 (3H, s), 5.51 (1H, br), 6.94 (1H, d, J=2 Hz), 7.29 (1H, d, J=2 Hz), 7.36 (1H, br), 8.05 (1H, s), 8.72 (1H, br).

(c) preparation of 4'-N-t-BOC-17-descarboxy-17-methoxypradimicin A

The general procedure described in example 2 (b) is repeated using oxazinone derivative 9 to provide the corresponding methoxy derivative.

(d) preparation of 4'-N-t-BOC pradimic acid amide

The general procedure described in example 2 (c) is repeated using the product of step (c) above to provide the title compound.

EXAMPLE 7

Preparation of Pradimicin D aglycone (10)

A mixture of 7 (50 mg, 0.10 mmol) and acetic anhydride (0.5 ml) in pyridine (2.5 ml) was heated for 1 day at 100° C. Toluene was added and the mixture was evaporated in vacuo. The residue was triturated with isopropyl ether to give a crude product, which was chromatographed on a column of silica gel (Wako-Gel C-200) using 5% MeOH CHCl$_3$ as eluant. Fractions containing the desired product were combined and concentrated, and the residue was triturated to give 40 mg of peracetylated pradimic acid amide aglycone.

Sodium hydride (60% suspension in mineral oil, 2.1 mg, 0.053 mmol) was added to a mixture of peracetylated pradimic acid amide aglycone (30 mg) in dry DMF (0.6 ml) and the mixture was stirred for 30 min. at room temperature. Ethyl iodoacetate (6 ml, 0.051 mmol) was added and the mixture was stirred for 3 days at room temperature. A mixture of 1N NaOH (1 ml) and MeOH (2 ml) was added to the pre-cooled mixture and stirred for 30 min at room temperature. After removal of MeOH, the mixture was chromatographed on a column of C$_{18}$ silica gel (Bondapak C$_{18}$, 20 i.d.×200 mm) and the column was eluted with 30–35% CH$_3$CN-water. The fractions containing the desired product was combined and concentrated in vacuo. The residue was acidified with dil. HCl and the precipitate was collected by centrifugation to provide 7.0 mg (yield 17%) of the title compound. The spectral date (IR, UV, NMR) and HPLC of this material were coincident with those of pradimicin D aglycone prepared from pradimicin D. MP >210° C. (dec).

EXAMPLE 8

Preparation of Pradimicin D (a) preparation of 4'-N-CBZ-pradimicin D (11)

A mixture of 4'-N-CBZ-pradimic acid amide (2) (15 mg, 0.017 mmol) and acetic anhydride (0.2 ml) in pyridine (1 ml) was heated under reflux overnight. After the solvent was removed in vacuo, the residue was triturated with ether-hexane to give 18 mg of peracetylated pradimic acid amide. To a solution of the peracetylated product (16.5 mg) in DMF (0.3 ml) was added NaH (1.8 mg, 0.045 mmol, ca 60% in oil). After the mixture was stirred for 30 min at room temperature, ethyl iodoacetate (5.5 $\mu$l, 0.046 mmol) was added and stirring continued for 5 hr at room temperature. The reaction mixture was poured into cold 0.1 N HCl, and extracted with EtOAc. The organic layer was washed with H$_2$O, dried over anhydrous Na$_2$SO$_4$ and concentrated in vacuo to give 21 mg of the amide alkylated product as a yellow oil. The oil was dissolved in 1N NaOH (1 ml) and MeOH (3 ml), and the mixture was stirred for 5 hr at room temperature. After MeOH was removed in vacuo, the mixture was diluted with H$_2$, acidified with 1N HCl and extracted with EtOAc. The resulting precipitate was collected by filtration, and combined with the organic layer. The solvent was removed under reduced pressure, and the residue was chromatographed on a C-18 silica gel column (Bondapak C$_{18}$, 10 i.d.×200 mm) eluting with 30–35% CH$_3$CN-H$_2$. The desired fractions were combined, evaporated, and lyophilized to give 4.2 mg (yield 28%) of pradimicin D. The spectral date (IR, UV, NMR) and HPLC of this material were coincident with those of 4'-N-CBZ pradimicin D prepared from pradimicin D. MP >230° C. (dec).

(b) preparation of pradimicin D (12)

To a mixture of 11 (4 mg) in MeOH (0.5 ml), AcOH (0.1 ml), and water (0.1 ml) was added and 10% palladium charcoal (1 mg) and the mixture was hydrogenated at room temperature. After filtration, the mixture was chromatographed on a column of Bondapak $C_{18}$. The column was eluted with 40% acetonitrile—pH 3.5 buffer. The fraction containing the desired product was concentrated in vacuo and desalted by using HP-20 column chromatography to give 3 mg of the product, of which spectral date (IR, UV, NMR) and HPLC were coincident with those of pradimicin D.

EXAMPLE 9

Preparation of 4'-N-CBZ-pradimic acid (13) (Method I)

A mixture of 4'-N-CBZ-pradimic acid amide 1 (196 mg, 0.22 mmol) and acetic anhydride (2 ml) in pyridine (10 ml) was stirred overnight at room temperature. After the solvent was removed under reduced pressure, the residue was triturated with isopropyl ether to give 260 mg of the peracetylated 4'-N-CBZ-pradimic acid amide. To a cold solution of this compound (260 mg) in acetonitrile (2.5 ml) were added $NOBF_4$ (61 mg, 0.52 mmol) and triethylamine (39 μl, 0.28 mmol). The mixture was stirred overnight at room temperature, cooled, treated with 1N NaOH (10 ml) for 1 hour, and then concentrated in vacuo. The residue was acidified with 1N HCl and the precipitate formed was collected by filtration. The filtrate was extracted with ethyl acetate, the organic layer was separated, concentrated, and combined with the precipitate. The crude mixture was chromatographed on a column of C-18 silica gel (Bondapak $C_{18}$, 20 i.d.×300 mm) using 30–40% acetonitrile-$H_2O$ as eluant. Fractions containing the desired compound were combined, concentrated, and lyophilized to give the title compound (40 mg, yield 20%) and the 4-nitro amide 14 (65 mg, yield 32%).

| M.P. AND SPECTRAL DATA FOR COMPOUND 13 | |
|---|---|
| M.P. (°C.) | >230 (grad. dec.) |
| IR (KBr) (cm$^{-1}$) | 1640–1680, 1600–1620 |
| UV (1/100N NaOH) | 320 (14,000) |
| $\lambda_{max}$ in nm (ε) | 502 (15,100) |
| FAB-MS (m/z) | 904 (M + H)$^+$ |
| $^1$H-NMR | 3.94 (3H, s) |
| 400 MHz | 6.86 (1H, d, J=2 Hz); 6.99 (1H, s); |
| DMSO-d$_6$ | 7.22 (1H, d, J=2 Hz); 8.04 (1H, s) |

EXAMPLE 10

Preparation of 4'-N-CBZ-pradimic acid (13) (Method II)

To a solution of 4'-N-CBZ-pradimic acid amide 2 (325 mg, 0.36 mmol), which had been dissolved in pyridine and dried in vacuo, in 1,4-dioxane (14 ml) were added $Bu_4NHSO_4$ (8 mg, 0.024 mmol), NaOH (powdered, 85 mg, 2.12 mmol) and acetyl chloride (82 μl, 1.15 mmol). The mixture was stirred for 30 minutes at room temperature, and the insoluble solid was removed by filtration. The filtrate was concentrated and the residue was triturated with isopropyl ether to give 247 mg of 1-O-acetyl 4'-N-CBZ-pradimic acid amide.

The above 1O-acetylated product was dissolved in pyridine (17 ml), and acetic anhydride (7 ml) was added. The reaction mixture was stirred overnight at room temperature, concentrated, and triturated with isopropyl ether to give 424 mg of the peracetylated 4'-N-CBZ-pradimic acid amide. To a cooled solution of this peracetylated product in acetonitrile (6 ml) was added $NOBF_4$ (105 mg, 0.90 mmol) and triethylamine (62 μl, 0.45 mmol). The reaction mixture was stirred overnight at room temperature and then cooled with an ice bath. To this mixture was added in NaOH (35 ml). After 1 hour at room temperature, acetonitrile was removed in vacuo and the residue was acidified with 1N HCl. The precipitate was collected by filtration and the filtrate was extracted with ethyl acetate. The organic layer was concentrated, combined with the precipitate and purified by C-18 silica gel (Bondapak $C_{18}$, 40 i.d.×450 mm) column chromatography using 30–40% acetonitrile-$H_2O$ as eluant. Fractions containing the desired compound were combined, concentrated, and lyophilized to give the title compound (131 mg, yield 40%).

EXAMPLE 11

Preparation of Pradimic Acid (15)

A mixture of 13 (37 mg, 0.041 mmol) in MeOH (2.2 ml), water (0.6 ml) and 10% palladium on charcoal (11 ml) was hydrogenated for 1.5 hours at room temperature. After removal of the catalyst, the mixture was chromatographed on a column of Bondapak $C_{18}$ (20 i.d.×200 mm) using 30–40% acetonitrile-water as eluant. Fractions containing the desired product were combined, concentrated and lyophilized to give 10.6 mg (34%) of the product.

| M.P. AND SPECTRAL DATA FOR COMPOUND 15 | |
|---|---|
| M.P. (°C.) | >230 (grad. dec.) |
| IR (KBr) (cm$^{-1}$) | 1620, 1600 |
| UV (1/100N NaOH) | 320 (10,300) |
| $\lambda_{max}$ in nm (ε) | 500 (11,000) |
| FAB-MS (m/z) | 770 (M + 1)$^+$ |
| $^1$H-NMR | 3.93 (3H, s) |
| 400 MHz | 4.52 (1H, d, J=10 Hz); 4.62 |
| DMSO-d$_6$ | (1H, dd, J=10 and 3 Hz); 6.80 |
|  | (1H, d, J=3 Hz); 6.93 (1H, s); 7.15 |
|  | (1H, d, J=3 Hz); 7.96 (1H, s) |

EXAMPLE 12

Synthesis of pradimicin A from 4'-CBZ-pradimic acid

A mixture of 4'-N-CBZ-pradimic acid 13 (53 mg, 0.059 mmol), 1-hydroxybenzotriazole (HOBT) (10 mg, 0.065 mmol), and dicyclohexylcarbodiimide (DCC) (15 mg, 0.073 mmol) in THF (1 ml) was stirred for 1 hr at room temperature. The reaction mixture was filtered to remove generated dicyclohexylurea, and to the filtrate was added a solution of D-alanine methyl ester hydrochloride (18 mg, 0.13 mmol) and (BSA) (140 μl, 0.57 mmol) in THF (0.5 ml). An additional amount of BSA (140 μl 0.57 ml) was added and the mixture was stirred overnight at room temperature. To the reaction mixture 1N HCl (2 ml) and MeOH (10 ml) were added. After stirring for 1 hr, 1N NaOH (3 ml) was added to the mixture. The mixture was stirred for 1 day, and then concentrated to ca. 5 ml. The concentrate was acidified with 1N HCl. The precipitate formed was collected by filtration and chromatographed on C-18 silica gel column (Bondapak $C_{18}$, 20 i.d.×400 mm) eluting with 20–30% acetonitrile-pH 3.5 buffer. The desired fractions were combined, concentrated and desalted by chromatography on a C-18 silica gel column using 30–40% acetonitrile-0.002N HCl as eluent to give 4'-N-CBZ-pradimicin A (11.5 mg, yield 20%) after lyophilization of the eluate.

A mixture of 4'-N-CBZ-pradimicin A (9 mg, 0.009 mmol) and 10% Pd—C (4 mg) in MeOH (2 ml)-1N HCl (0.2 ml) was stirred under $H_2$ atmosphere for 120 min at room temperature. The Pd—C was removed by filtration and the filtrate was concentrated to ca. 1 ml. The concentrate was chromatographed on a C-18 silica gel column (Bondapak $C_{18}$, 20×400 nun) eluting with 10–20% acetonitrile-0.001N HCl. The fractions containing the desired compound were combined, concentrated, and lyophilized to give 7.6 mg (yield 94%) of pradimicin A as an amorphous powder, which was identical to naturally occurring pradimicin A in spectroscopic data (NMR, IR, UV), HPLC and antifungal activity.

EXAMPLE 13

15-Desalanyl-15-[D-(3,4-dihydroxyphenyl)alanyl] pradimicin A

A mixture of 13 (52 mg, 0.058 mmol), HOBT (10 mg, 0.065 mmol) and DCC (16 mg, 0.079 mmol) in THF (2 ml) was stirred for 1 hour at room temperature and filtered to remove resulting dicyclohexyl urea. The filtrate was concentrated and the residue was dissolved in 1 ml of 50% aqueous dioxane. To the mixture was added a solution of D-3,4-dihydroxyphenylalanine (D-DOPA) (24 mg, 0.12 mmol) and triethylamine (20 μl, 0.14 mmol) in 1 ml of 50% aqueous dioxane. The mixture was stirred for 1 day at room temperature and then dioxane was removed under reduced pressure. To the residue was added 50 ml of $H_2O$ and the mixture was acidified with 1N HCl to pH 2. The precipitate formed was collected by filtration and chromatographed on a column of C-18 silica gel (Bondpak $C_{18}$, 20 i.d.×200 mm). The column was eluted with 30–40% acetonitrile-1/1000N HCl and the desired fraction was concentrated and lyophilized to give 4'N-CBZ protected title compound (23 mg, yield 37%).

A mixture of the above compound (20 mg, 0.018 mmol) and 10% Pd—C (9 mg) in MeOH (2 ml)-N HCl (0.4 ml) was hydrogenated at atmospheric pressure for 90 min at room temperature. In order to hydrolyze methyl ester of the product generated during catalytic hydrogenation, 1N NaOH (2 ml) was added and the mixture was stirred for 30 min at room temperature. The catalyst was removed by filtration and the filtrate was acidified with 1N HCl. The mixture was concentrated to volume of ca. 1 ml and chromatographed on a column of silica gel (Bondapak $C_{18}$, 20 i.d.×200 mm). The column was eluted with 20% acetonitrile-1/1000N HCl and the fractions containing the desired product were combined, concentrated and lyophilized to give 7.2 mg (yield 41%) of the title compound (13H). MP >70° C. (grad dec); IR 1620 cm$^{-1}$, UV; $\lambda_{max}$ 320 nm ($\epsilon$13,500), 500 nm (12,800); FAB-MS 949 (M+H)$^+$.

EXAMPLE 14–20

Synthesis of New Pradimicin Derivatives

The general procedures described in Examples 12 and 13 were repeated using the amino acid starting materials listed below instead of the amino acid derivatives used therein to provide the corresponding product of the following formula:

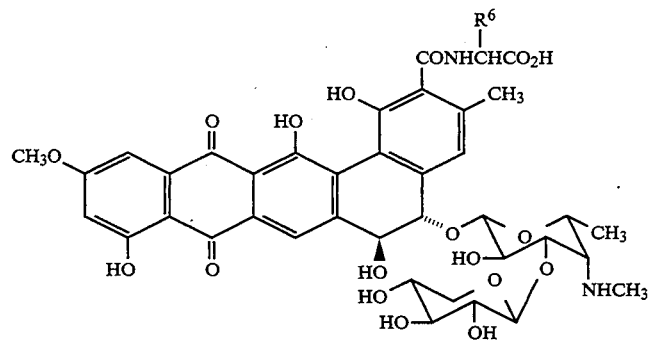

| Ex. | starting material | R$^6$ | phys. properties |
|---|---|---|---|
| | | Method of Example 12 | |
| 14 | (L)-serine | (L) CH$_2$OH | MP: >210° C. (grad dec) |
| | | | IR: 1600 cm$^{-1}$ |
| | | | UV: 320 (11,700), |
| | | | 497 (12,400) |
| | | | FAB-MS: 857 |
| 15 | (D)-2,3-diamino-propanoic acid | (D) CH$_2$NH$_2$ | MP: >210° C. (grad dec) |
| | | | IR: 1620 cm$^{-1}$ |
| | | | UV: 320 (7,900), |
| | | | 498 (8,100) |
| | | | FAB-MS: 856 |
| 16 | (D)-aspartic acid | (D) CH$_2$CO$_2$H | MP: 175° C. (grad dec) |
| | | | IR: 1720, 1620 cm$^{-1}$ |
| | | | UV: 322 (10,700), |
| | | | 498 (10,900) |
| | | | FAB-MS: 885 |
| | | Method of Example 13 | |
| 17 | (DL)-trifluoro-alanine | (DL) CF$_3$ | MP: >210° C. (dec) |
| | | | IR: 1620 cm$^{-1}$ |
| | | | UV: 322 (10,200), |
| | | | 499 (10,300) |
| | | | FAB-MS: 895 |
| 18 | (D)-phenylalanine | (D) CH$_2$Ph | MP: >210° C. (grad dec) |
| | | | IR: 1600–1620 cm$^{-1}$ |
| | | | UV: 320 (9,900), |

| Ex. | starting material | R⁶ | phys. properties |
|---|---|---|---|
| | | | 498 (10,500) |
| | | | FAB-MS: 917 |
| 19 | (D)-histidine | (D) imidazol-5-yl-methyl | MP: >200° C. (grad dec) |
| | | | IR: 1600 cm$^{-1}$ |
| | | | UV: 322 (10,600), |
| | | | 502 (11,300) |
| | | | FAB-MS: 907 |
| 20 | 5-aminomethyl-tetrazole | * | MP: >190° C. (grad dec) |
| | | | IR: 1600–1640 cm$^{-1}$ |
| | | | UV: 320 (9,100), |
| | | | 497 (9,200) |
| | | | FAB-MS: 851 |
| 21 | (D)-Lysine | (D) $(CH_2)_4NH_2$ | MP: >200° C. |
| | | | IR: 1600–1640 cm$^{-1}$ |
| | | | UV: 321 (14,000), |
| | | | 500 (14,800) |
| | | | FAB-MS: 898 |
| 22 | (D)-Arginine | (D) $(CH_2)_3NHC(=NH)NH_2$ | MP: >210° C. (grad. dec.) |
| | | | IR: 1600–1640 cm$^{-1}$ |
| | | | UV: 319 (12,000), |
| | | | 495 (10,600) |
| | | | FAB-MS: 841 |
| 23 | (D)-Cysteine | (D) $CH_2SCONHEt$ | MP: >220° C. (grad. dec.) |
| | | | IR: 1600–1640 cm$^{-1}$ |
| | | | UV: 247 (13,900), |
| | | | 498 (7,370) |
| | | | FAB-MS: 944 |

*NHCH(R⁵)CO₂H =

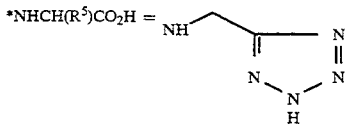

EXAMPLE 24

4'-desmethylamino-4'-hydroxypradimic acid amide (16)

A mixture of 4'-desmethylamino-4'-hydroxypradimicin A (846 mg, 1.02 mmol), triethylamine (0.4 ml, 2.89 mmol) and diphenylphosphoryl azide (DPPA, 821 mg, 2.98 mmol) in 40 ml of DMF and 40 ml of t-BuOH was heated under reflux for 4 hours. Insoluble solid (the starting material recovered) was removed by filtration and washed with a small amount of DMF. The filtrate was concentrated and the residue was dissolved in 160 ml of MeOH and 80 ml of 1N aq. NaOH. Stirring was continued for 1 hour at room temperature, the mixture was concentrated to the volume of ca. 50 ml. The alkaline solution was added dropwise to a cold solution of 160 ml of 6N HCl and 320 ml of CH₃CN. The mixture was stirred for 30 minutes at ice-bath temperature and then CH₃CN was removed under reduced pressure. Precipitates appeared in the mixture were collected by filtration and washed with water. The crude solid was purified by C₁₈ silica gel (Bondapak C₁₈, 40 i.d.×600 mm) column chromatography eluted with CH₃CN—phosphate buffer (pH 7.0, 12.5–15%, gradient). Fractions containing the desired compound were combined and concentrated. The concentrate was acidified with 1N HCl and resulting precipitates were collected by centrifugation and dried under reduced pressure to give 543 mg (Yield: 70%) of 4'-desmethylamino-4'-hydroxypradimic acid amide (16).

Mp. >230° C. (grad. dec.) IR $\nu_{max}$ (KBr)cm$^{-1}$ 1600, 1640 UV $\lambda_{max}$ (0.01N NaOH) nm (ε) 315(9,500), 499 (9,900) MS(FAB) 756 (M+H)³⁰ ¹H NMR (DMSO-d₆) δ1.10 (3H, d, J=6 Hz), 2.34 (3H, s), 3.70 (1H, dd, J=5 & 11 Hz), 3.96 (3H, s), 4.40 (1H, d, J=7 Hz), 4.49 (1H, d, J=10 Hz), 4.58 (1H, d, J=10 Hz), 4.63 (1H, d, J=7 Hz), 6.96 (1H, d, J=3Hz), 7.16 (1H, s), 7.31 (1H, d, J=3 Hz), 7.56 (1H, brs), 7.66 (1H, brs), 8.06 (1H, s).

EXAMPLE 25

Preparation of 4'-desmethylamino-4'-hydroxypradimic acid (17)

A mixture of 4'-desmethylamino-4'-hydroxypradimic acid amide (16, 410 mg, 0.54 mmol), pyridine (0.2 ml, 2.47 mmol), acetic acid (93 μl, 1.62 mmol) and dicyclohexylcarbodiimide (334 mg, 1.62 mmol) in 4 ml of dry DMF and 20 ml of dry dioxane was stirred overnight at room temperature. Resulted solids were removed by filtration and the filtrate was concentrated under reduced pressure. To the residue were added 40 ml of pyridine and 8 ml of acetic anhydride. Stirring was continued for 4 hours at room temperature and then the mixture was azeotropically evaporated with toluene. The residue was triturated with hexane to give 689 mg of peracetylated compounds. To a cold solution of these compounds (689 mg) in dry CH₃CN (10 ml) were added NOBF₄ (147 mg, 1.26 mmol) and Et₃N (98 μl 0.71 mmol). The mixture was stirred overnight at room temperature, cooled, treated with 10 ml of 2N NaOH for 3 hours, and then concentrated in vacuo. The concentrate was acidified with 10% citric acid and resulted precipitate was collected by filtration. The crude solid was purified by C₁₈ silica gel (Bondapak C₁₈, 40 i.d.×600 mm) column chromatography using 12.5–15% CH₃CN—pH 7 buffer as eluent. After concentrating the desired fractions, the residue was acidified by addition of 6N HCl. The precipitate formed was collected by centrifugation, washed with water and lyophilized to give 181 mg (Yield: 44%) of the title compound. Mp. >230° C. (grad. dec.) IR $\nu_{max}$ (KBr)cm$^{-1}$ 1710, 1610 UV $\lambda_{max}$ (0.01N NaOH) nm (ε) 224(29,000), 274 (25,400), 314 (sh, 10,800), 507(12,700) MS(FAB) 757

(M+H)+ ¹H NMR (DMSO-d₆) δ6 1.10 (3H, d, J=6 Hz), 2.54 (3H, s), 3.69 (1H, dd, J=5 & 11 Hz), 3.95 (3H, s), 4.40 (1H, d, J=7 Hz), 4.52 (1H, d, J=10 Hz), 4.60–64 (2H, m), 6.63 (1H, d, J=3 Hz), 7.18 (1H, s), 7.29 (1H, d, J=3Hz), 8.03 (1H, s).

EXAMPLE 26

An alternative preparation of 4'-desmethylamino-4'-hydroxypradimic acid (17)

A mixture of 4'-desmethylamino-4'-hydroxypradimicin A (860 mg, 1.04 mmol), triethylamine (0.4 ml, 2.89 mmol) and diphenylphosphoryl azide (DPPA, 838 mg, 3.05 mmol) in 40 ml of dimethylformamide and 40 ml of t-BuOH was heated under reflux for 4 hours. Insoluble solids were removed by filtration and the filtrate was concentrated to dryness. The solid was triturated with 10% citric acid and filtered. The resulting solid (oxazinone) was collected and dissolved in MeOH —2N NaOH (4:1, 200 ml). The mixture was stirred overnight at room temperature and then concentrated to the volume of ca. 20 ml. The alkaline solution was added dropwise to cold 6N HCl—CH₃CH (1:2, 480 ml). Stirred for 2 hours at room temperature, the mixture was concentrated under reduced pressure. The resulting precipitates were collected by filtration, washed with water and dried in vacuo to give 764 mg of crude 4'-desmethylamino-4'-hydroxypradimic acid amide (16). This crude 16 was used in the next step without further purification.

A mixture of the above crude 4'-desmethylamino-4'-hydroxypradimic acid amide (764 mg), pyridine (0.3 ml, 3.7 mmol), acetic acid (0.14 ml, 2.4 mmol) and dicyclohexylcarbodiimide (510 mg, 2.5 mmol) in dimethylformamide-dioxane (1:5, 36 ml) was stirred for 3.5 hours at room temperature. Dicyclohexylurea precipitated was removed by filtration and the filtrate was azeotropically evaporated with toluene. To the residue containing the 1-O-acetylated product was added pyridine (40 ml) and AC₂O (8 ml). The solution was stirred for 2 hours at room temperature and concentrated. The residue was triturated with hexane to give 930 mg of peracetylated 4'-desmethylamino-4'-hydroxypradimic acid amide. To a cold solution of the peracetylated product in 15 ml of dry CH₃CN were added nitrosoniumtetrafluoroborate (NOBF₄, 243 mg, 2.08 mmol) and triethylamine (148 μl, 1.07 mmol) under argon atmosphere. The mixture was stirred overnight at room temperature and then cooled in an ice-bath. To the mixture was added 10 ml of 2N NaOH. After stirring for 2 hours at room temperature, the mixture was evaporated in vacuo and the residue was acidified by addition of 6N HCl. The precipitate was collected by filtration and purified by C₁₈ silica get (Bondapak C₁₈, 40 i.d.×600 mm) column chromatography. The column was eluted with 10–15% CH₃CN—pH 7 phosphate buffer. The fractions containing 4'-desmethylamino-4'-hydroxypradimic acid were collected, concentrated to the volume of ca. 100 ml and acidified by addition of 1N HCl. The resulting precipitate was collected, washed with water and lyophilized with 10% aq. dioxane to give 375 mg (Yield: 48%) of 4'-desmethylamino-4'-hydroxypradimic acid (17). The physico-chemical data of this product were quite identical with those of the compound 17 in Example 25.

EXAMPLE 27

15-Desalanyl-15-(D-threonyl)-4'-desmethylamino-4'-hydroxypradimicin A

A mixture of 4'-desmethylamino-4'-hydroxypradimic acid (17, 50 mg, 0.066 mmol), 1-hydroxybenzotriazole (15 mg, 0.098 mmol) and dicyclohexylcarbidiimide (20 mg, 0.097 mmol) in 0.5 ml of DMF and 1.5 ml of THF was stirred for 1 hour at room temperature and then concentrated. The concentrate was dissolved in 1 ml of dioxane—H₂O (2:1). A mixture of (D)-threonine (16 rag, 0.16 mmol) and triethylamine (54 μl, 0.39 mmol) in 1 ml of dioxane—H₂O (2: 1) was added to the above solution. Stirred overnight at room temperature, the mixture was concentrated by evaporation in vacuo. The concentrate was dissolved in 1 ml of 2N NaOH and chromatographed on a column of C₁₈ silica get (Bondapak C₁₈, Waters, 40 i.d.×200 mm). Elution with 10–15% CH₃CN—pH 7 phosphate buffer afforded fractions containing the desired product, which were combined, concentrated and desalted by C₁₈ silica gel (Bondapak C₁₈, Waters, 20 i.d.×200 mm) column chromatography to afford the title compound (19 mg, Yield: 34%). Mp. >210° C. (grad. dec.) IR $\nu_{max}$ (KBr)cm⁻¹ 1620 UV $\lambda_{max}$ (0.01N NaOH) nm (ε) 319 (13,800), 497 (13,700) MS(FAB) 859 (M+H)+ ¹H NMR (DMSO-d₆) δ6 1.11 (3H, d, J=6 Hz), 1.19 (3H, d, J=6 Hz), 2.33 (3H, s), 3.70 (1H, dd, J=5 & 11 Hz), 4.17 (1H, m), 4.39 (1H, d, J=7 Hz), 4.41 (1H, dd, J=3 & 8 Hz), 4.49 (1H, d, J=11 Hz), 4.56 (1H, d, J=11 Hz), 4.64 (1H, d, J=8 Hz), 6.92 (1H, d, J=2 Hz), 7.17 (1H, s), 7.28 (1H, d, J=2 Hz), 7.94 (1H, d, J=8 Hz), 8.03 (1H, s).

| Method of Example 27 | | | |
| --- | --- | --- | --- |
| Ex. | starting material | R⁶ | phys. properties |
| 17 | (D)-F—Ala | (L) CH₂F | MP: >250° C. (grad. dec.) IR: 1610 cm⁻¹ UV: 318 (15,900), 495 (14,700) FAB-MS: 846 |
| 29 | (D)-Cystine | (D) CH₂S—S—CH₂(NH₂)COOH | MP: >210° C. (grad. dec.) IR: 1620 cm⁻¹ UV: 274 (21,700), 500 (10,600) FAB-MS: 979 |
| 30 | (L)-Ser | (L) CH₂OH | MP: >210° C. (grad. dec.) IR: 1620 cm⁻¹ UV: 321 (12,900), 497 (12,900) FAB-MS: 844 |
| 31 | (D)-Ala | (D) CH₃ | MP: >220° C. (grad. dec.) IR: 1623 cm⁻¹ UV: 319 (12,900), 498 (12,200) FAB-MS: 828 |

We claim:

1. A process for the preparation of a compound having the formula

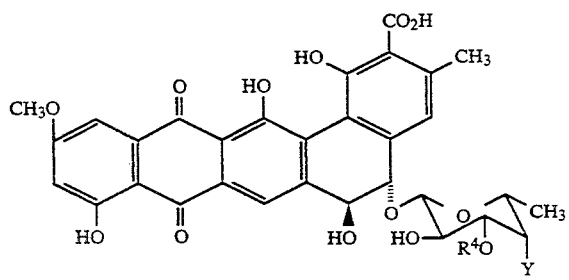

wherein Y is OH or $NR^2R^3$; $R^2$ is hydrogen or methyl; $R^3$ is hydrogen, $C_{1-5}$ alkyl, or an amino protecting group; $R^4$ is hydrogen, hydroxy protecting group, or β-D-xylosyl; which comprises (a) treating a compound having the formula

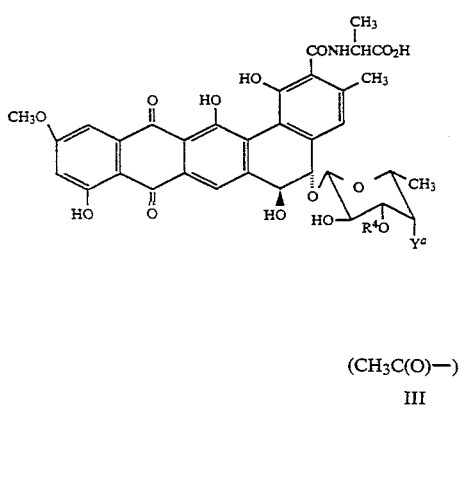

wherein $Y^a$ is OH or $NR^{2a}R^{3a}$; $R^{2a}$ is hydrogen or methyl, $R^{3a}$ is $C_{1-5}$ alkyl or an amino protecting group with the proviso that when $R^{2a}$ is hydrogen $R^{3a}$ is an amino protecting group; and $R^4$ is hydrogen, β-D-xylosyl or a hydroxy protecting group; with diphenylphos- phoryl azide in the presence of a base; (b) treating the product formed in step (a) with alkaline aqueous alcohol; (c) hydrolyzing the product formed in step (b) under acidic conditions; and (d) optionally replacing the protecting groups with hydrogen.

2. A process for the preparation of a compound having the formula

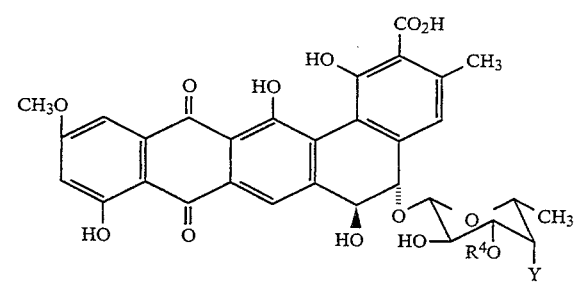

wherein Y is OH or $NR^2R^3$; $R^2$ is hydrogen or methyl; $R^3$ is hydrogen, $C_{1-5}$ alkyl, or an amino protecting group; $R^4$ is hydrogen, hydroxy protecting group, or β-D-xylosyl; which comprises (a) treating a compound of the formula

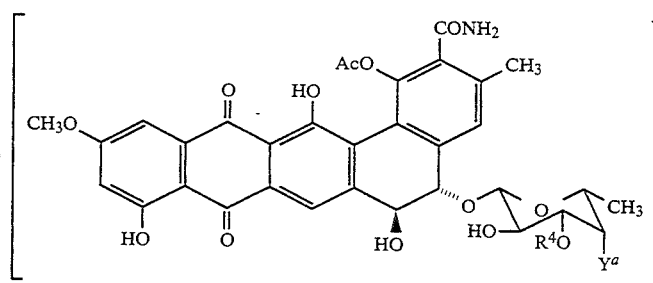

wherein $Y^a$ is OH or $R^{2a}R^{3a}$; $R^{2a}$ is hydrogen or methyl, $R^{3a}$ is $C_{1-5}$ alkyl or an amino protecting group with the proviso that when $R^{2a}$ is hydrogen $R^{3a}$ is an amino protecting group; and $R^4$ is hydrogen, β-D-xylosyl, or a hydroxy protecting group, m is an integer from 1 to 6, Ac is acetyl; with a reagent selected from the group consisting of nitrosonium tetrafluoroborate, nitrosyl chloride, butyl nitrite, sodium nitrite, and nitrogen tetraoxide; (b) removing the acetyl groups; and (c) optionally removing the protecting groups.

3. The process of claim 2 wherein the reagent is nitrosonium tetrafluoroborate.

* * * * *